United States Patent [19]

Sandler

[11] Patent Number: 4,845,270

[45] Date of Patent: Jul. 4, 1989

[54] PROPANONE 1,3-DISULFONIC ACID AS AN ESTERIFICATION CATALYST

[75] Inventor: Stanley R. Sandler, Springfield, Pa.

[73] Assignee: Pennwalt Corporation, Philadelphia, Pa.

[21] Appl. No.: 173,408

[22] Filed: Mar. 25, 1988

[51] Int. Cl.$^4$ ............................................. C07C 69/52
[52] U.S. Cl. ........................................ 560/205; 560/98; 560/204; 560/265; 260/410.9 R
[58] Field of Search ................. 560/205, 98, 204, 265; 260/410.9 R

[56] References Cited

U.S. PATENT DOCUMENTS

| | | | |
|---|---|---|---|
| 3,071,604 | 1/1963 | Mohan et al. | 260/410.6 |
| 3,354,199 | 11/1967 | Lachowicz et al. | 560/205 |
| 3,776,947 | 12/1973 | Shimizu et al. | 560/205 |
| 4,340,546 | 7/1982 | Qualeatti et al. | 560/205 |
| 4,748,269 | 5/1988 | Meixner et al. | 560/205 |

FOREIGN PATENT DOCUMENTS 767145  9/1967  Canada ................................ 560/208
70392  6/1968  German Democratic Rep. .

OTHER PUBLICATIONS

Zey, E. G., "Esterification", *Kirk–Othmer Encyclopedia of Chemical Technology*, 3rd ed., vol. 9, pp. 291–310, John Wiley & Sons, New York, 1978.
Grot, W. G., *J. Org. Chem.*, 30, 515-7 (1965).

*Primary Examiner*—Paul J. Killos
*Attorney, Agent, or Firm*—Bernard F. Plantz

[57] ABSTRACT

The present invention discloses the use of propanone 1,3-disulfonic acid as an esterification catalyst. This catalyst has a significantly higher reaction rate when compared to conventional esterification catalysts, such as methanesulfonic acid and sulfuric acid.

10 Claims, 1 Drawing Sheet

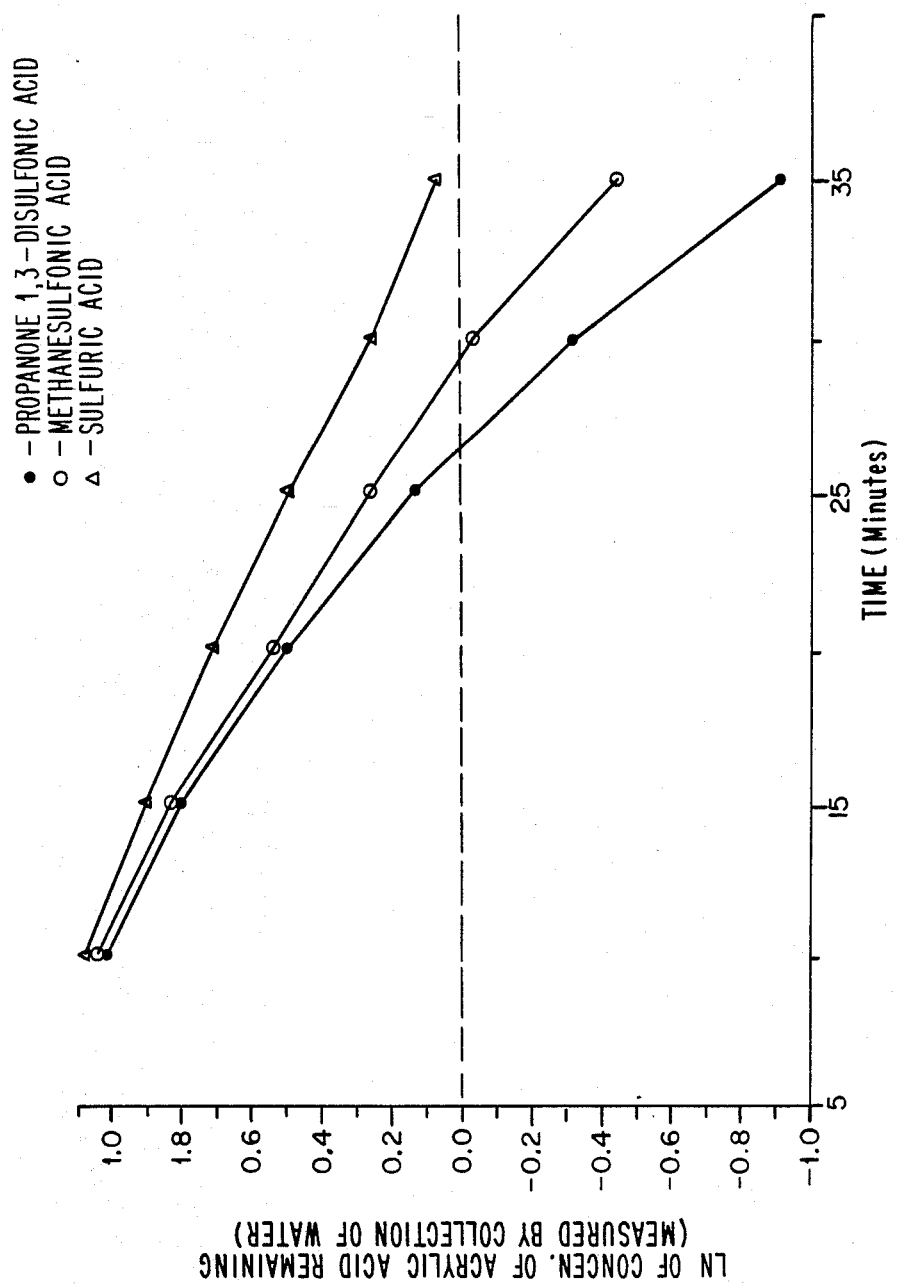

PROPANONE 1,3-DISULFONIC ACID AS AN ESTERIFICATION CATALYST

BACKGROUND OF THE INVENTION

The present invention relates to the use of propanone 1,3-disulfonic acid, also more commonly known as acetone disulfonic acid, as an esterification catalyst.

The reaction of an organic acid with an alcohol to produce the corresponding acid ester is generally well known. These esterification reactions are typically carried out in the presence of an acid catalyst. E. G. Zey in the chapter entitled "Esterification" in the *Kirk-Othmer Encyclopedia of Chemical Technology*, 3rd ed., Volume 9, pp. 291–310, John Wiley & Sons, New York, 1978 discloses that the most common catalysts are strong mineral acids, but other agents, such as tin salts, organotitanates, silica gel and cation-exchange resins, are often employed. Sulfuric acid and hydrochloric acid are the classical esterification catalysts for laboratory preparations. However, alkyl chlorides may form or dehydration, isomerization, or polymerization side reactions may result when these acids are used. Sulfonic acids, such as benzenesulfonic acid, p-toluenesulfonic acid, or methanesulfonic acid, are often used in plant operations because they are less corrosive. Phosphoric acid has also been used, but it leads to rather slow reactions.

U.S. Pat. No. 3,071,604 issued Jan. 1, 1963 to A. G. Mohan et al. discloses the esterification of saturated and unsaturated fatty acids with monohydric and polyhydric alcohols. The acid catalysts which are disclosed as being effective in the esterification reactions include alkyl, aryl, or alkylaryl sulfonic acids, which include methanesulfonic acid, benzenesulfonic acid, p-toluenesulfonic acid, and dodecylbenzenesulfonic acid. Inorganic acids, such as sulfuric acid, phosphoric acid and sulfonic acid-type ion-exchange resins are also disclosed as catalysts.

Although there are several known acids which function as esterification catalysts, there is a continuing need, especially on a commerical scale, for a catalyst with a more rapid rate of ester product formation.

SUMMARY OF THE INVENTION

The present invention includes a method of esterifying a carboxylic acid with an alcohol in the presence of a catalytically effective amount of propanone 1,3-disulfonic acid to form the corresponding carboxylic acid ester. Propanone 1,3-disulfonic acid has a first order rate constant which is significantly higher than that for sulfuric acid or methanesulfonic acid.

BRIEF DESCRIPTION OF THE DRAWING

The FIGURE is a plot of the natural logarithm of the moles of acrylic acid remaining at time t versus time t for the esterification reactions of Examples 1–3.

DETAILED DESCRIPTION OF THE PREFERRED EMBODIMENTS

The esterification catalyst of the present invention, propanone 1,3-disulfonic acid, can be prepared by a variety of techniques. Applicant's copending U.S. patent application Ser. No. 044,933, filed May 1, 1987, which is hereby incorporated by reference, describes a method for preparing propanone 1,3-disulfonic acid. This method involves the reaction of chlorosulfonic acid with acetone in the presence of methylene chloride. The reaction product is purified by washing the solid product with methylene chloride, and a solution is then prepared by adding water. Propanone 1,3-disulfonic acid can also be prepared by the sulfonation of acetone with fuming sulfuric acid or oleum, W. Grot, *J. Org. Chem.*, 30, 515–7 (1965) and German Democratic Republic Patent No. 70,392 issued June 28, 1968 to F. Wolf.

The carboxylic acids useful in the present invention include both saturated and unsaturated carboxylic acids which are conventionally esterified with an alcohol. Such acids include saturated fatty acids, such as acetic acid, as well as unsaturated fatty acids, such as acrylic acids. In addition to monocarboxylic acids, dicarboxylic acids, such as maleic acid, succinic acid and adipic acid, may be used with the esterification catalyst of the present invention. The carboxylic acids useful in the present invention may also include aromatic acids, such as phthalic acid and terephthalic acid. Generally, the carboxylic acid contains up to about 18 carbon atoms and may have substituents, such as halogen, which do not interfere with the esterification reaction.

The alcohols useful in the present invention include both monohydroxy alcohols, such as methanol, and dihydroxy alcohols, such as ethylene glycol. The alcohols generally contain up to about 30 carbon atoms and may contain substituents which do not interfere with the esterification reaction, such as halogen, ether, or nitro groups. These alcohols may be saturated as well as unsaturated.

The esterification reaction of the present invention may be represented by the following equation:

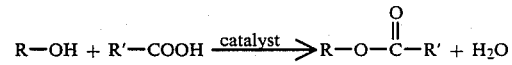

This reaction may be carried out in a solvent, such as cyclohexane, by heating and collecting the water which is evolved in a Dean and Stark type trap. The reaction temperature is generally in the range of about 80° to about 250° C. When other higher boiling point solvents are utilized, the reaction temperature is typically higher. The reaction shown above may also be carried out using an excess amount of the alcohol as the solvent. In many instances, the solvent forms an azeotrope with the water by-product which must be removed from the ester product by azeotropic distillation.

Propanone 1,3-disulfonic acid is generally present in amounts ranging from about 0.01 to about 0.05 equivalent per equivalent carboxylic acid. A preferred range of the catalyst is between about 0.01 to about 0.02 equivalent per equivalent carboxylic acid.

The following examples illustrate the increased reaction rates which were achieved when the esterification catalyst of the present invention was employed. Propanone 1,3-disulfonic acid (Example 1), methanesulfonic acid (Example 2) and sulfuric acid (Example 3) were used as the esterification catalysts in the preparation of 2-ethylhexylacrylate from 2-ethylhexanol and acrylic acid. This reaction is represented by the following equation:

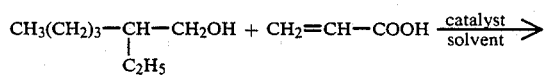

-continued

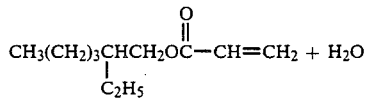

The reaction was carried out using cyclohexane as a solvent. The amount of water which was evolved during the reaction was directly related to the amount of acrylic acid which was consumed. As shown in the FIGURE, the rate constant was calculated by plotting the value of natural logarithm of the moles of acrylic acid remaining at time t against time t, and then obtaining the slope of the line for the points shown. This slope is the first order rate constant.

EXAMPLE 1

A flask, equipped with a magnetic stirrer, water cooled condenser with a drying tube, heating mantle and a thermocouple, was filled with 37.3 grams (g) of acrylic acid (0.5 mole of 96.6% assay), 71.7 g of 2-ethylhexanol (0.55 mole of 99.9% assay), 37.2 g of cyclohexane, 0.5 g hydroquinone, as a polymerization inhibitor, and 2.1 g (as an aqueous solution containing 54.0% by weight; 0.01 equivalents) of propanone 1,3-disulfonic acid as the esterification catalyst. The reaction mixture was stirred and heated at 94°–105° C. for 1.5 hours while the water which was evolved during the reaction was collected in a trap by azeotroping with cyclohexane. The cumulative amount of water which was evolved over a time period of 10–35 minutes is shown below in Table 1.

EXAMPLE 2

The same equivalent amount of methanesulfonic acid (1.4 g of a 70% solution) was substituted for propanone 1.3-disulfonic acid in Example 1. The same equipment, reactants other than the catalyst, and reaction conditions were utilized. The cumulative amount of water which was evolved over a time period of 10–35 minutes is shown in Table 1.

EXAMPLE 3

The same equivalent amount of sulfuric acid (0.5 g of 95.4% sulfuric acid) was substituted for propanone 1,3-disulfonic acid as the esterification catalyst in Example 1. The same equipment, reaction conditions, and reactants, other than the esterification catalyst, were utilized. The cumulative amount of water which was evolved over a time period of 10–35 minutes is shown in Table 1.

TABLE 1

| Time (min.) | Water Evolved (ml.) | | |
|---|---|---|---|
| | Example 1 | Example 2 | Example 3 |
| 10 | 2.56 | 2.40 | 2.14 |
| 15 | 3.82 | 3.70 | 3.28 |
| 20 | 5.20 | 5.05 | 4.30 |
| 25 | 6.35 | 6.00 | 5.20 |
| 30 | 7.30 | 6.75 | 6.00 |
| 35 | 8.05 | 7.50 | 6.50 |

Based on the amount of water which was evolved, the amount of acrylic acid that remained at time t was calculated. As shown in the FIGURE, the natural logarithm of the moles of acrylic acid remaining at time t was plotted against time t. The slope of the line for these points was then calculated and is reported in Table 2, shown below, as the experimental first order rate constant.

TABLE 2

| Example | Catalyst | Rate Constant K (moles/liter-sec.) |
|---|---|---|
| 1 | Propanone 1,3-disulfonic acid | $1.26 \times 10^{-3}$ |
| 2 | Methanesulfonic acid | $9.7 \times 10^{-4}$ |
| 3 | Sulfuric acid | $6.8 \times 10^{-4}$ |

It was unexpectedly found, based on the rate constant, that the esterification reaction using propanone 1,3-disulfonic acid was about 30% fasteer than the esterification reaction which used methanesulfonic acid as the catalyst. Furthermore, the esterification reaction using propanone 1,3-disulfonic acid was 85% faster than the esterification reaction employing sulfuric acid as the esterification catalyst. These results clearly illustrate that the esterification catalyst of the present invention produces the product ester at a faster rate which is significant in the commerical production of esters.

The Examples shown above are not considered to limit the present invention, but are only illustrative of the increased reaction rate which is achieved with the use of the esterification catalyst of the present invention. Esterification reactions other than those used in the production of 2-ethylhexylacrylate are considered within the scope of the present invention.

I claim:
1. A method of esterifying a carboxylic acid with an alcohol comprising:
   reacting a carboxylic acid with an alcohol in the presence of a catalytically effective amount of propanone 1,3-disulfonic acid to form the corresponding carboxylic acid ester.
2. A method according to claim 1 wherein said carboxylic acid contains up to about 18 carbon atoms.
3. A method according to claim 1 wherein said alchohol contains up to about 30 carbon atoms.
4. A method according to claim 1 wherein said reaction is carried out in the presence of a solvent.
5. A method according to claim 1 wherein said reaction is carried out in the presence of an excess amount of said alcohol which is used as a solvent.
6. A method according to claim 1 wherein said carboxylic acid is acrylic acid and said alcohol is 2-ethylhexanol.
7. A method according to claim 6 wherein said reaction is carried out at a temperature in the range of about 80 to about 250° C.
8. A method according to claim 7 wherein the water by-product is removed from the reaction products by azeotropic distillation.
9. A method according to claim 8 wherein cyclohexane is used as the solvent for the azeotropic distillation and removal of the water by-product.
10. A method according to claim 8 wherein excess 2-ethylhexanol is used as the solvent for the azeotropic distillation and removal of the water by-product.

* * * * *